US010571377B2

(12) United States Patent
Greenfield et al.

(10) Patent No.: US 10,571,377 B2
(45) Date of Patent: Feb. 25, 2020

(54) TORSION TESTING MACHINE AND METHODS FOR ADDITIVE BUILDS

(71) Applicant: Delavan Inc., West Des Moines, IA (US)

(72) Inventors: Jacob Greenfield, Granger, IA (US); Thomas J. Ocken, Des Moines, IA (US); Jerry Logsdon, Van Meter, IA (US); Lukas Shea, Carlisle, IA (US)

(73) Assignee: Delavan Inc., West Des Moines, IA (US)

( * ) Notice: Subject to any disclaimer, the term of this patent is extended or adjusted under 35 U.S.C. 154(b) by 0 days.

(21) Appl. No.: 16/031,224

(22) Filed: Jul. 10, 2018

(65) Prior Publication Data

US 2020/0018675 A1 Jan. 16, 2020

(51) Int. Cl.
*G01N 3/00* (2006.01)
*G01N 3/26* (2006.01)
*G01N 3/06* (2006.01)

(52) U.S. Cl.
CPC ............ *G01N 3/26* (2013.01); *G01N 3/066* (2013.01); *G01N 2203/0021* (2013.01); *G01N 2203/0268* (2013.01)

(58) Field of Classification Search
CPC .. G01N 3/26; G01N 3/066; G01N 2203/0021; G01N 2203/0266
USPC .......................................................... 73/791
See application file for complete search history.

(56) References Cited

U.S. PATENT DOCUMENTS

| 5,567,884 | A | * | 10/1996 | Dickinson | ................ G01N 3/20 |
| | | | | | 73/814 |
| 6,030,709 | A | * | 2/2000 | Jensen | .................... C23C 30/00 |
| | | | | | 338/25 |
| 7,165,465 | B2 | | 1/2007 | De Lair et al. | |
| 8,845,316 | B2 | | 9/2014 | Schillen et al. | |
| 9,188,675 | B2 | * | 11/2015 | Bulea | .................. H03K 17/955 |
| 9,555,475 | B2 | | 1/2017 | Sidhu et al. | |
| 9,689,783 | B2 | | 6/2017 | Dietrich et al. | |
| 9,903,781 | B2 | | 2/2018 | Drescher et al. | |
| 2015/0021832 | A1 | | 1/2015 | Yerazunis et al. | |
| 2016/0169821 | A1 | | 6/2016 | Meyer et al. | |
| 2016/0349134 | A1 | * | 12/2016 | Jeon | ......................... G01L 1/14 |

(Continued)

FOREIGN PATENT DOCUMENTS

| CN | 107389447 A | 11/2017 |
| DE | 102016201289 A1 | 8/2017 |

(Continued)

OTHER PUBLICATIONS

Extended European Search Report issued in corresponding EP application No. 19185268.0 dated Nov. 27, 2019.

*Primary Examiner* — Max H Noori
(74) *Attorney, Agent, or Firm* — Locke Lord LLP; Daniel J. Fiorello; Scott D. Wofsy

(57) ABSTRACT

A system can include a torsion applicator (e.g., a torsion motor and shaft) configured to apply a torque to a test article that is additively built on and attached to a build plate. The system can include at least one twist sensor and at least one torque sensor. A method for determining quality of an additively manufactured article or batch thereof can include torsion testing at least one additively manufactured test article that is built on and attached to a build plate while the at least one test article is still attached to the build plate.

14 Claims, 7 Drawing Sheets

(56) References Cited

U.S. PATENT DOCUMENTS

| | | |
|---|---|---|
| 2017/0136695 A1 | 5/2017 | Versluys et al. |
| 2018/0072000 A1* | 3/2018 | Riemann ................ B33Y 10/00 |
| 2018/0086004 A1* | 3/2018 | Van Espen ............. B33Y 40/00 |
| 2018/0088559 A1* | 3/2018 | Salem ................ G05B 19/4099 |
| 2018/0188144 A1* | 7/2018 | Deal .................... B29O 64/386 |
| 2019/0105839 A1* | 4/2019 | Hicks .................... B29C 64/379 |
| 2019/0118300 A1* | 4/2019 | Penny ................... B29C 64/393 |
| 2019/0143406 A1* | 5/2019 | Carter ..................... B22F 3/003 |

FOREIGN PATENT DOCUMENTS

| | | |
|---|---|---|
| EP | 2698619 A1 | 2/2014 |
| JP | 3437052 B2 | 8/2003 |
| WO | WO-2012048982 A1 | 4/2012 |
| WO | WO-2018052297 A1 | 3/2018 |

\* cited by examiner

TORSION TESTING MACHINE AND METHODS FOR ADDITIVE BUILDS

BACKGROUND

1. Field

The present disclosure relates to additive manufacturing, more specifically to material property testing for additive manufactured articles.

2. Description of Related Art

There is a need to verify material properties of each additively built article. Traditionally, there is a long lead time between the time of growing the plate of parts and when traditional material testing can be completed on test bars from that plate. This requires increased effort and cost be added to the parts before even knowing if the material properties are ultimately acceptable.

The current method for verifying material properties of additively manufactured articles is to complete tensile testing. Test bars are built with each build. Tensile testing cannot be completed until the test bars have been removed from the plate and machined to the proper dimensions for testing. This requires the build plate to go through all of the required post processing before the testing is completed. By the time the testing is completed a new build has started and much value has been added to the parts.

Such conventional methods and systems have generally been considered satisfactory for their intended purpose. However, there is still a need in the art for improved verification methods and devices to verify material properties earlier in the process. The present disclosure provides a solution for this need.

SUMMARY

In accordance with at least one aspect of this disclosure, a torsion testing machine for additively manufactured test articles can include at least one build plate holder configured to allow insertion of and retention of a build plate therein, at least one torsion motor, and at least one torsion shaft configured to operatively connect to the torsion motor. The at least one torsion shaft can be configured to mate with at least one test article built on and attached to the build plate when the build plate is in the build plate holder. The at least one torsion motor can be configured to apply a torsion to the at least one test article through the torsion shaft while the build plate is retained in the build plate holder. The machine can include at least one torque sensor operatively connected to the torsion applicator to determine a torque applied by the torsion motor to the test article.

The machine can include at least one strain gauge operatively connected to the at least one torsion applicator to determine a twist on the torsion shaft. In certain embodiments, the machine can include at least one motor sensor configured to measure a position of the torsion motor. In certain embodiments, the machine can include a data acquisition system operatively connected to the torque sensor and the strain gauge, for example, and configured to compare the torque and the twist to known data to determine a condition of the test article and/or other articles built on the build plate.

The torsion motor can be mounted to a movable assembly to allow the torsion motor to be repositioned relative to the build plate holder to allow the shaft to mate with a test article located in a plurality of discreet positions or located in any position on the build plate. The moveable assembly can include an adjustable rail system allowing the motor to slide on one or more rails. The machine can include one or more quick release clamps to selectively lock the motor to the one or more rails.

The machine can include a part catching tray located under the build plate holder for catching fractured parts. The machine can include an enclosure enclosing at least the torsion motor, the torsion shaft, the build plate holder.

In certain embodiments, the torsion shaft can include a lower sleeve socket for receiving a socket head of the test article. The torsion shaft can be configured to removably connect to a motor shaft such that the torsion shaft allows positioning of the build plate under the torsion motor and to allow the sleeve socket to be slid over the test article before and/or after insertion of the build plate.

The torsion shaft can include an upper socket for receiving the motor shaft. The upper socket and the motor shaft can interface together via a removable connection, for example. The removable connection can be a ball detent, for example.

In accordance with at least one aspect of this disclosure, a system can include a torsion applicator (e.g., a torsion motor and shaft) configured to apply a torque to a test article that is additively built on and attached to a build plate. The system can include at least one twist sensor and at least one torque sensor.

The system can include a data acquisition system configured to receive torque data from the at least one torque sensor and twist data from the at least one twist sensor. The data acquisition system can be configured to compare the torque data and twist data to known expected data. The data acquisition system can be configured to output a plot of torque versus twist.

In accordance with at least one aspect of this disclosure, a method for determining quality of an additively manufactured article or batch thereof can include torsion testing at least one additively manufactured test article that is built on and attached to a build plate while the at least one test article is still attached to the build plate. Torsion testing can include applying a torque to the test article using a torsion testing machine while the build plate is retained in the torsion testing machine.

The method can include removing the build plate from an additive manufacturing machine and inserting the build plate into the torsion testing machine. The method can include retaining the build plate in the torsion testing machine.

The method can include additively manufacturing the at least one test article on the build plate to have a test head configured to be torqued by a socket. The test head can include a hex shape, for example, or any other suitable shape.

The at least one test article can include a narrow body, for example. The method can include sensing a torque on the at least one test article and/or a twist on the at least one test article to create torque data and/or twist data.

The method can include comparing the torque data and/or twist data to known expected data to determine a quality of the at least one test article. The method can include plotting and displaying torque versus twist on an electronic display.

Torsion testing can include torsion testing the at least one test article until the at least one test article breaks. The method can include catching debris from the broken test article in a part catching tray.

Torsion testing the at least one additively manufactured test article can be performed while the build plate is still in an additive manufacturing machine. Torsion testing the at least one additively manufactured test article can be performed prior to completion of additive manufacture of the additively manufactured article or batch thereof in the additive manufacturing machine.

In accordance with at least one aspect of this disclosure, a method can include additively manufacturing a test article on a build plate to include a test head shaped to be torqued by a socket. Additively manufacturing the test article can include forming a base of the test article to adhere to the build plate such that the base of the test article remains attached to the build plate throughout torsion testing.

Additively manufacturing the test article can include forming a narrow body attached to the head and the base such that the narrow body fails before the base detaches from the build plate. Additively manufacturing the test article can include forming the base to have a wide area contacting the build plate to enhance adherence to the build plate.

The wide area can include a disc shape contacting the build plate, for example, or any other suitable shape. Forming the test head can include forming a hex head configured to be torqued by a standard socket wrench, for example, or any other suitable shape.

These and other features of the systems and methods of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION

Figure 1A:
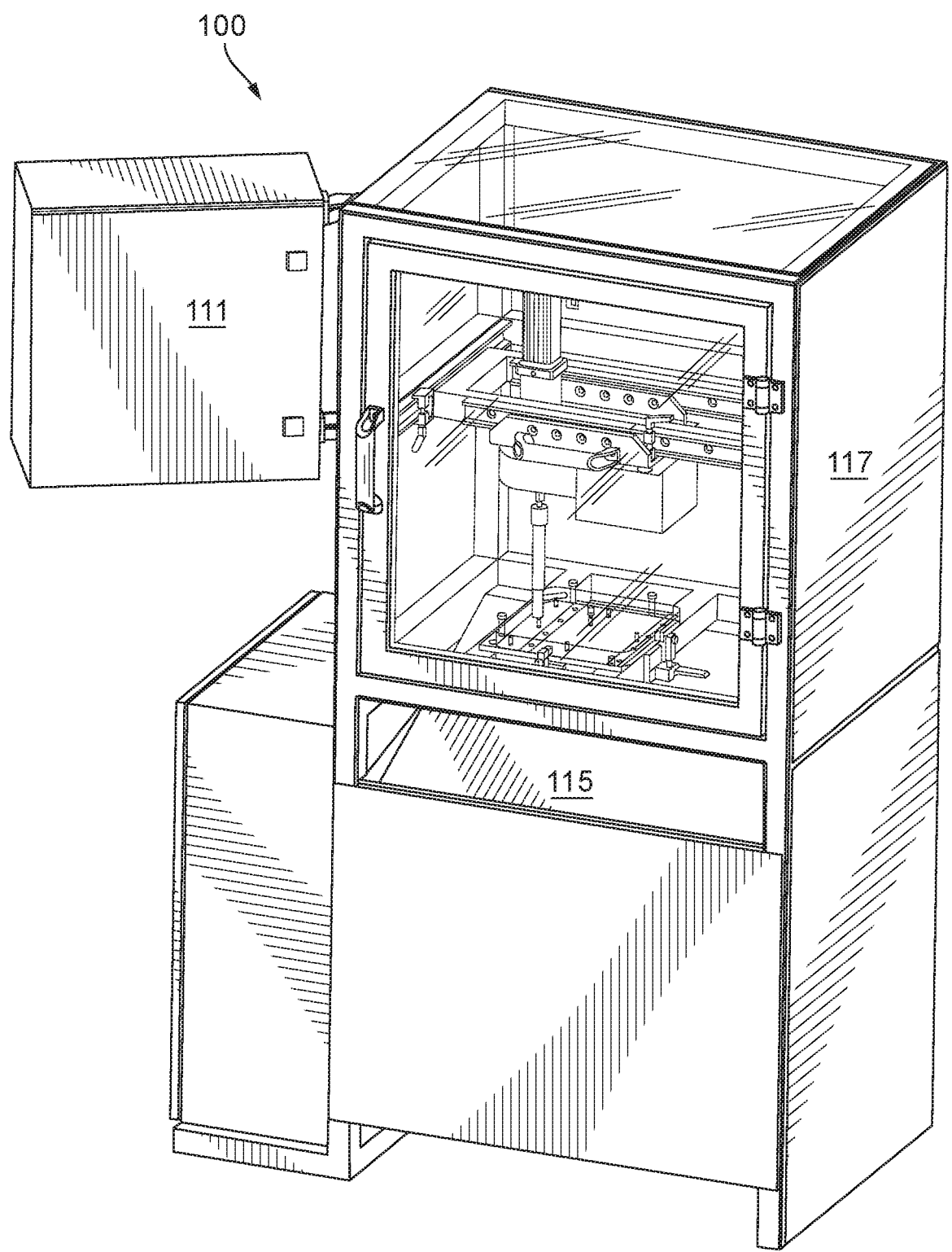
FIG. 1A is a perspective view of an embodiment of a machine in accordance with this disclosure.
Figure 1B:
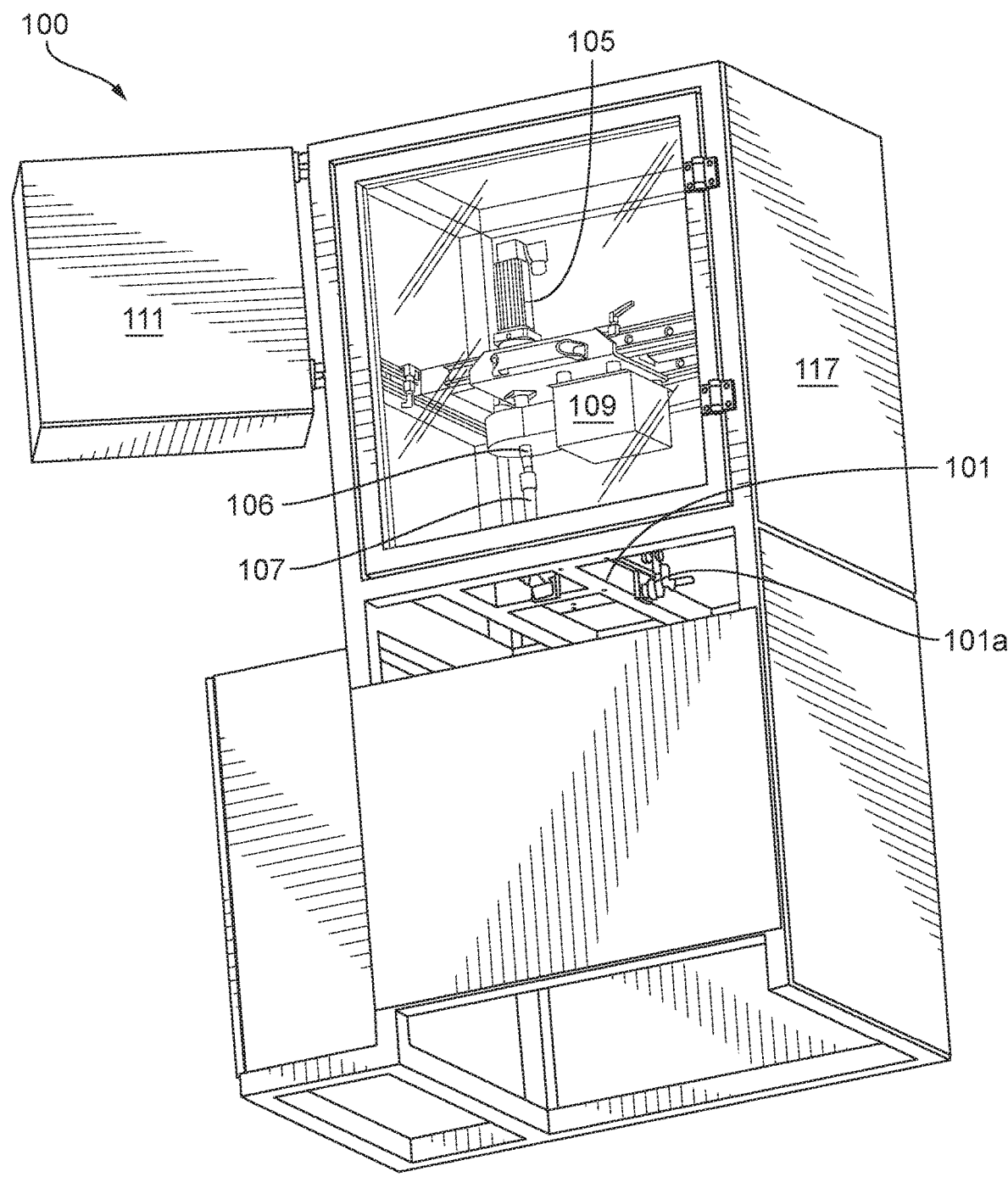
FIG. 1B is a perspective view of the embodiment of FIG. 1.
Figure 1C:
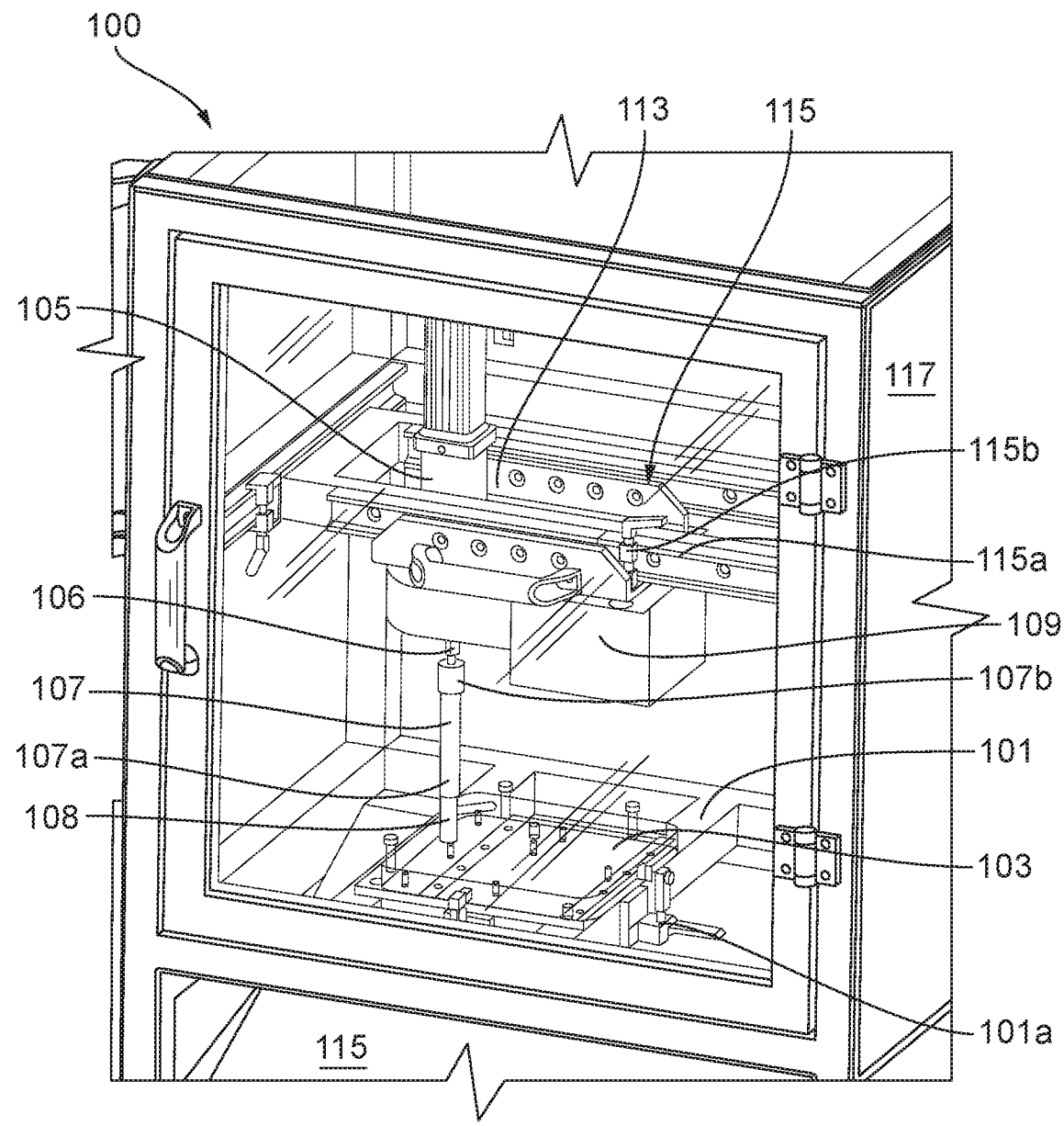
FIG. 1C is a close up perspective view of the embodiment of FIG. 1.

Reference will now be made to the drawings wherein like reference numerals identify similar structural features or aspects of the subject disclosure. For purposes of explanation and illustration, and not limitation, an illustrative view of an embodiment of a machine in accordance with the disclosure is shown in FIGS. 1A-1C and is designated generally by reference character 100. Other embodiments and/or aspects of this disclosure are shown in FIGS. 2-7.

In accordance with at least one aspect of this disclosure, referring to FIGS. 1A-1C, a torsion testing machine 100 for additively manufactured (e.g., selective laser sintered) test articles (e.g., as shown in FIGS. 2-8 built) can include at least one build plate holder 101 configured to allow insertion of and retention of a build plate 103 therein. The build plate holder 101 can include any suitable fastener(s) to retain the build plate 103 therein (e.g., clamps 101a or one or more screws configured to interface with existing screw holes in the build plate 103). In certain embodiments, the build plate holder 101 can include a slot configured to receive the build plate 103 such that it that retains the build plate 103 with or without one or more fasteners.

The machine 100 can include at least one torsion motor 105 (e.g., and electric motor) and at least one torsion shaft 107 configured to operatively connect to the torsion motor 105. The at least one torsion shaft 105 can be configured to mate with at least one test article (e.g., test article 108) built on and attached to the build plate 103 when the build plate 103 is in the build plate holder 101.

The at least one torsion motor 105 can be configured to apply a torsion to the at least one test article 108 through the torsion shaft 107 while the build plate 103 is retained in the build plate holder 101. The machine 100 can include at least one torque sensor 109 operatively connected to the torque motor 105 to determine a torque applied by the torsion motor 105 to the test article 108. The torque sensor 109 may be wireless and configured to communicate with a data acquisition system (e.g., as described below). Any suitable torque sensor 109 as appreciated by those having ordinary skill in the art is contemplated herein.

In certain embodiments, the machine 100 can include at least one strain gauge (not specifically shown) operatively connected to the at least one torque motor 105 to determine a twist on the torsion shaft 107 and/or the test article 108. For example, the strain gauge can be attached to the shaft between the torque motor and the test article 108. The strain gauge can be integrated into the torque sensor 109, and/or can be wireless, for example.

In certain embodiments, the machine 100 can include at least one motor sensor (not shown), e.g., within the motor, configured to measure a position of the torsion motor 105. The motor 105 can be configured to sense position as appreciated by those having ordinary skill in the art. In certain embodiments, the machine 100 can include a data acquisition system 111 operatively connected to the torque sensor 109 and the strain gauge, for example, and configured to compare the torque and the twist to known data to determine a condition of the test article 108 and/or other articles built on the build plate 103. The data acquisition system 111 can also be configured to control the motor 105 and/or any other suitable portions of the machine 100 (e.g., a mechanized positioning system). The data acquisition system 111 can include any suitable computer hardware and/or software.

The torsion motor 105 (and/or the build plate holder 101) can be mounted to a movable assembly 113 to allow the torsion motor 105 to be repositioned relative to the build plate holder 101 to allow the shaft 107 to mate with a test article 108 located, e.g., in a plurality of discreet positions or located in any position on the build plate. The moveable assembly 113 can include an adjustable rail system 115 allowing the motor 105 (e.g., and anything attached thereto such as the torque sensor 109) to slide on one or more rails 115a. The machine 100 can include one or more quick release clamps 115b to selectively lock the motor 105 to the one or more rails 115a. While the motor 105 is shown moveable, it is contemplated that, either additionally or alternatively, the build plate holder 101 and/or the build plate 101 can be moveable relative to the motor 105 in any suitable manner to allow connection of the shaft 107 and the test article 108. While embodiments are shown having motion available in 2 dimensions, it is contemplated that the moveable assembly 113 can be configured to move in any suitable number of dimensions (e.g., in the additional 3rd up down dimension).

In certain embodiments, the machine 100 can include a part catching tray 115 located under the build plate holder 101 for catching fractured test parts and/or any other suitable debris. In certain embodiments, the machine 100 can include an enclosure 117 enclosing at least the torsion motor 105, the torsion shaft 107, and the build plate holder 101. Any other suitable enclosing structure is contemplated herein. In certain embodiments, the machine 100 can be integrated into an additive manufacturing machine, and a separate structure may be unnecessary.

Figure 2:
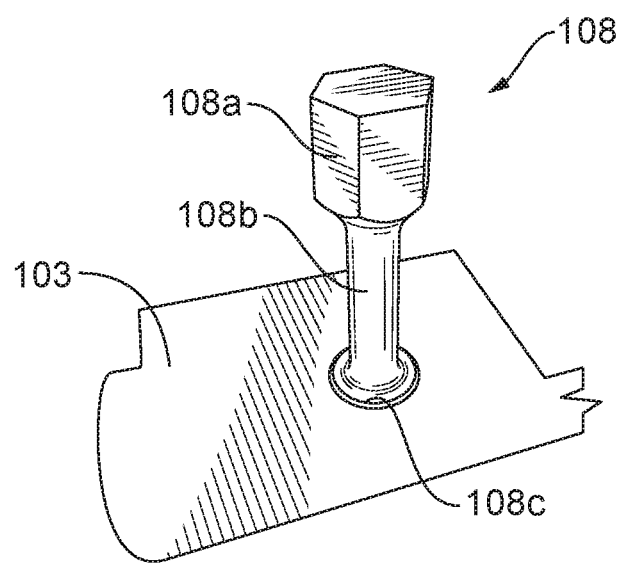
FIG. 2 is a perspective view of an embodiment of a test article formed on and attached to a build plate in accordance with this disclosure.
Figure 3:
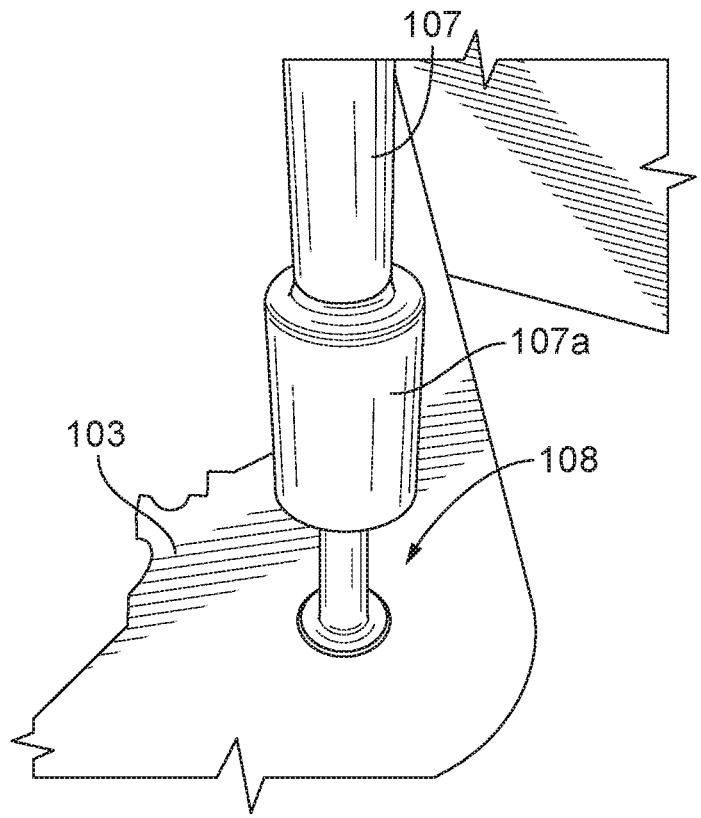
FIG. 3 is a perspective view of the embodiment of the test article of FIG. 2 in torsion testing.

In certain embodiments, referring additionally to FIGS. 2 and 3, the torsion shaft 107 can include a lower sleeve socket 107a for receiving a socket head 108a of the test article 108. The torsion shaft 107 can be configured to removably connect to a motor shaft 106 (which can be any shaft of the motor 105 or any shaft connected directly or indirectly thereto, e.g., a torque sensor shaft) such that the torsion shaft 107 allows positioning of the build plate 103 under the torsion motor 103 and to allow the sleeve socket 107a to be slid over the test article 108 before and/or after insertion of the build plate 103.

In certain embodiments, the torsion shaft 107 can include an upper socket 107b (e.g., as shown in FIG. 1C, for receiving the motor shaft 106. The upper socket 107b and the motor shaft 106 can interface together via a removable connection, for example. The removable connection can be a ball detent, for example (e.g., as in a socket wrench connector, or similar).

In accordance with at least one aspect of this disclosure, embodiments include a system (e.g., a machine 100) that include a torsion applicator (e.g., a torsion motor 105 and shaft 107) configured to apply a torque to a test article 108 that is additively built on and attached to a build plate 103. The system can include at least one twist sensor (e.g., a strain gauge) and at least one torque sensor (e.g., sensor 109 with integrated strain gauge).

The system can include a data acquisition system (e.g., system 111 as described above) configured to receive torque data from the at least one torque sensor and/or twist data from the at least one twist sensor. The data acquisition system can be configured to compare the torque data and twist data to known expected data. The data acquisition system can be configured to output a plot of torque versus twist. The plot can be displayed on any suitable display for a user to inspect and/or determine a quality of the test article, and hence one or more articles built on the build plate.

In certain embodiments, the data acquisition system can be configured process the torque data and/or the twist data and to determine a quality of an additively manufactured part (e.g., the test article or another part from the same batch) based on the torque and/or twist data. In view of this disclosure, one having ordinary skill in the art would understand how to empirically develop, without undue experimentation, known data to compare the torque data and twist data against to determine a quality of the additive manufacturing part.

Figure 4:
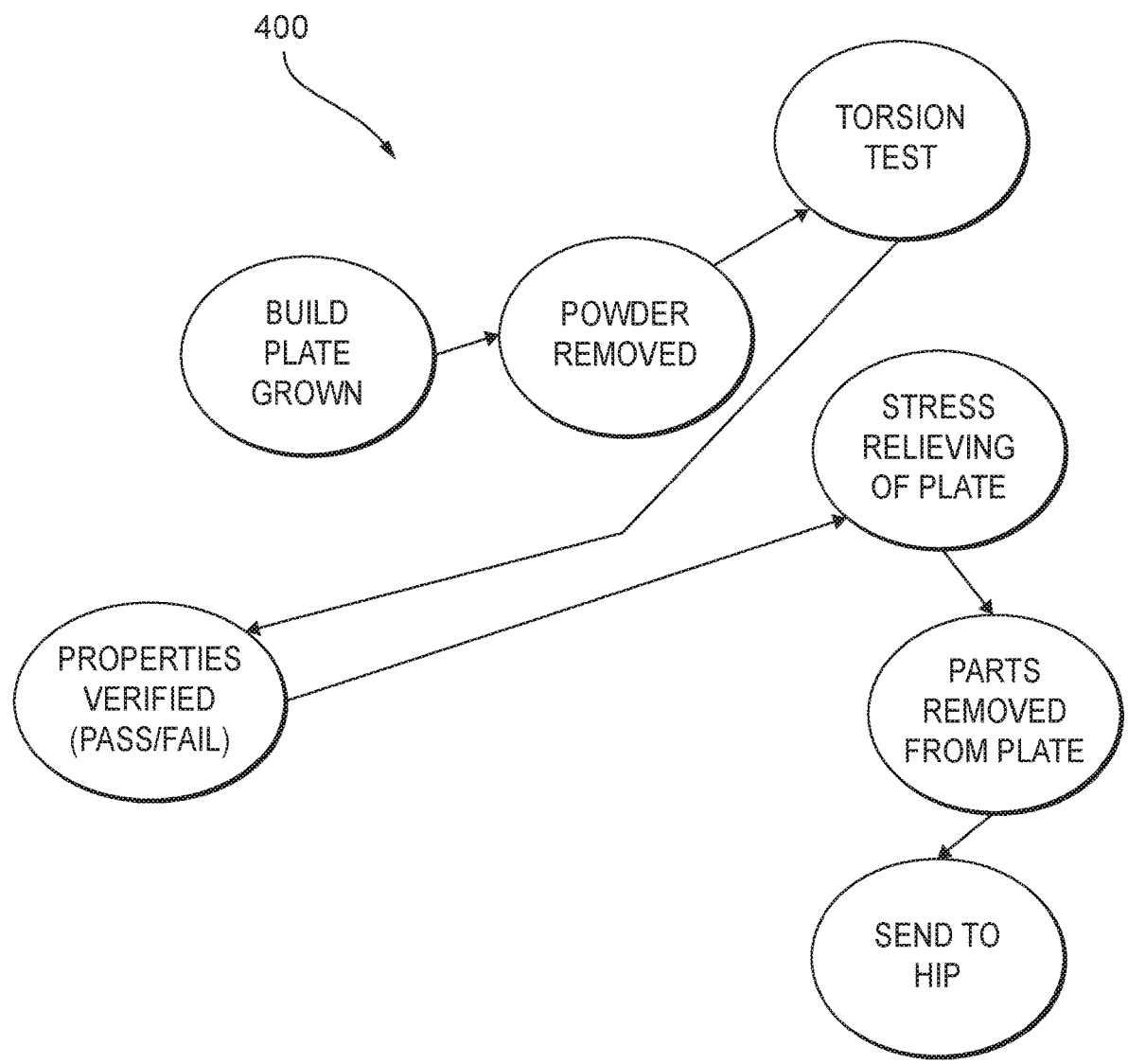
FIG. 4 is flow diagram of an embodiment of a method in accordance with this disclosure.

Referring additionally to FIG. 4, in accordance with at least one aspect of this disclosure, a method for determining quality of an additively manufactured article or batch thereof can include torsion testing at least one additively manufactured test article that is built on and attached to a build plate while the at least one test article is still attached to the build plate. The method 400 can include any other suitable portions, certain examples being described below and/or certain examples being shown in FIG. 4. For example, torsion testing can include applying a torque to the test article using a torsion testing machine while the build plate is retained in the torsion testing machine.

The method 400 can include removing the build plate from an additive manufacturing machine and inserting the build plate into the torsion testing machine. The method 400 can include retaining the build plate in the torsion testing machine.

Figure 5:
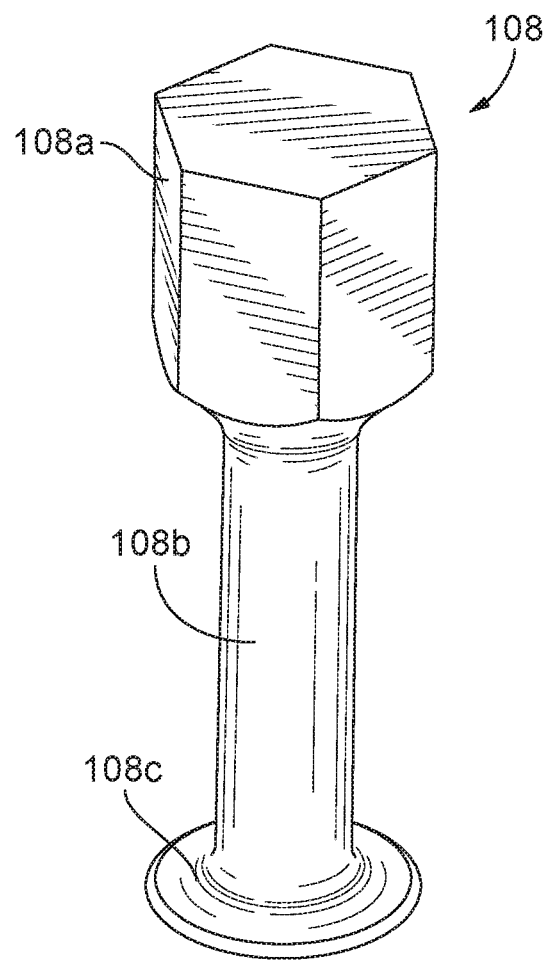
FIG. 5 is a perspective view of an embodiment of a test article in accordance with this disclosure.
Figure 6:
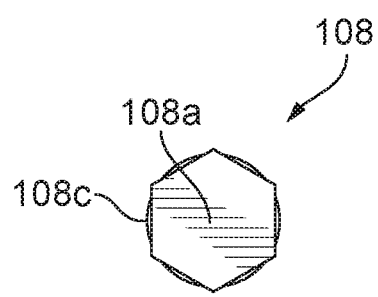
FIG. 6 is a plan view of the embodiment of FIG. 5.
Figure 7:
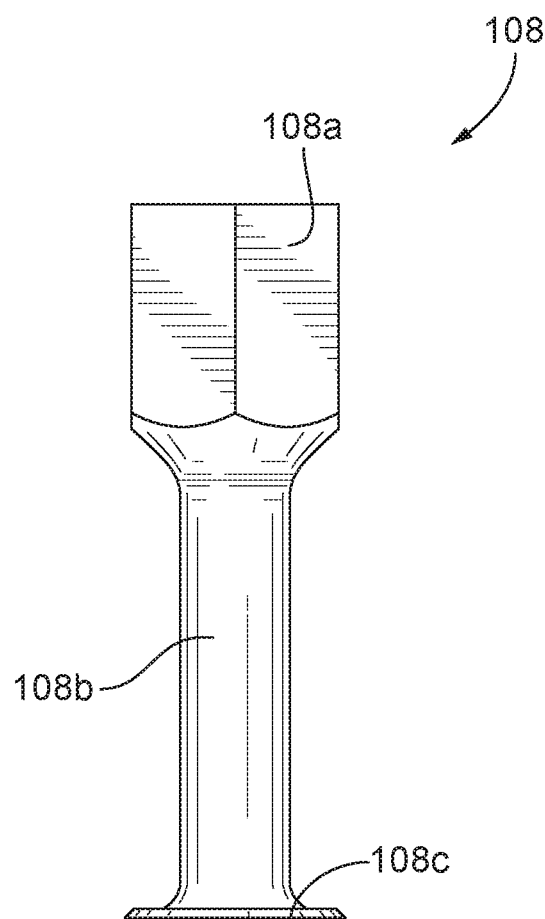
FIG. 7 is a side elevation view of the embodiment of FIG. 5.

Referring additionally to FIGS. 5-7, the method 400 can include additively manufacturing the at least one test article (e.g., test article 108) on the build plate to have a test head (e.g., test head 108a) configured to be torqued by a socket (e.g., lower sleeve socket 107a of torsion shaft 107). The test head (e.g., test head 108a) can include a hex shape, for example, or any other suitable shape.

The at least one test article (e.g., test article 108) can include a narrow body (e.g., body 108b), for example. For example, the at least one test article can be shaped to adhere to the ASTM E8/E8M standard for round tensile testing bars (e.g., the gauge section diameter can be about 25% of the gauge section length). The method 400 can include sensing a torque on the at least one test article and/or a twist on the at least one test article to create torque data and/or twist data.

The method 400 can include comparing the torque data and/or twist data to known expected data to determine a quality of the at least one test article. For example, if torque vs. twist data is within a suitable predetermined range of values of the expected value, the quality can be determined to be acceptable (e.g., by the data acquisition system and/or by a user). The data acquisition system can provide an indication regarding the quality (e.g., an alarm when quality is unacceptable). In certain embodiments, the method can include plotting and displaying torque versus twist on an electronic display, for example.

Torsion testing can include torsion testing the at least one test article until the at least one test article breaks. The method can include catching debris from the broken test article in a part catching tray.

Torsion testing the at least one additively manufactured test article (e.g., test article 108) can be performed while the build plate is still in an additive manufacturing machine. Torsion testing the at least one additively manufactured test article can be performed prior to completion of additive manufacture of the additively manufactured article or batch thereof in the additive manufacturing machine.

In accordance with at least one aspect of this disclosure, referring to FIGS. 2, 3, and 5-7, a method can include additively manufacturing a test article 108 on a build plate 103 to include a test head 108a shaped to be torqued by a socket. Additively manufacturing the test article 108 can include forming a base 108c of the test article 108 to adhere to the build plate 103 such that the base of the test article 108 remains attached to the build plate 103 throughout torsion testing.

Additively manufacturing the test article can include forming a narrow body 108b attached to the head 108a and the base 108c such that the narrow body 108b fails before the base 108c detaches from the build plate 103. Additively manufacturing the test article 108 can include forming the base 108c to have a wide area (e.g., at least as wide as the head 108a) contacting the build plate 103 to enhance adherence to the build plate 103.

The wide area base 108c can include a disc shape contacting the build plate 103, for example, or any other suitable shape. Forming the test head 108a can include forming a hex head configured to be torqued by a standard socket wrench, for example, or any other suitable shape.

Embodiments include a torque testing machine that can allow for a new method (embodiments disclosed herein) of quality testing to be used. The torsion sample can be built and tested on the plate. Embodiments allow for proper testing inputs of strain rate along with proper measurement of the outputs of torque and strain. Embodiments of a torsion testing machine also allow for the variation in torque sample location on the plate. Embodiments reduced lead time from growth of a plate of parts to verification of material properties of the grown parts. Embodiments enable an accurate and controlled testing environment with accurate and recordable data output, for example.

Embodiments include a torsion sample (e.g., a test article 108) and testing method (e.g., method 400) that can be completed on the build plate, e.g., right after powder removal. The torsion sample can be grown on the plate in such a way that one or more embodiments of a torsion testing machine (e.g., embodiments disclosed herein) can be used to test the material. Embodiments utilize a test method and specimen that can be completed directly on the plate prior to all post processing of the plate other than powder removal, which can allows the material properties to be verified prior to adding effort and cost into the post processing of the plate.

For example, in certain embodiments, a short sample can be grown directly on the plate, already to the dimensions needed for torsion testing (e.g., a test article with a hex head which can fit within a testing machine as described above). Adjustable systems as described hereinabove can allow for gauge section diameter (e.g., diameter of the torsion shaft 107) and/or height (e.g., of the torsion shaft) to be adjusted as needed.

Embodiments allow immediate feedback on potential machine failure to reduce exposure to in process parts which can speed up the manufacturing process by eliminating process steps needed for tensile testing, for example. The removed portion of the test article can be utilized for other material verification needs, i.e. hardness, surface roughness, porosity, grain size, chemistry, etc.

Certain embodiments of a torsion testing machine can include a frame (e.g., extruded t-slot aluminum rails), a build plated mount (which can be fixed or moveable, and may be configured to handle various plate sizes), a torque sensor with wireless strain gauge, displacement and/or torque controlled motor on adjustable rails, a data acquisition system with the ability to transfer data, an HMI visual control system with preset programs to control input variables, a part catcher, and the ability to output a Torque-Twist diagram which can allow the verification of material properties via ASTM E143-13 methods.

The motor and torque sensor can be mounted to the adjustable rail system which can be configured to allow the motor and sensor to be moved forward and backward, as well as left to right, for example. This can give embodiments of the machine the capability to test a torque specimen at any location on the build plate. Quick release clamps can be used to lock the motor and sensor in place once lined up with a sample, and also to lock the plate in place to the build plate mount when connected to the torque tester. Certain embodiments of the data acquisition system can collect the torque-twist data and can give the operator a quick pass/fail check as well as output the data for further use. Embodiments can include a safety enclosure to meet safety requirements, and/or a full interlock system on a door of the enclosure.

As will be appreciated by those skilled in the art, aspects of the present disclosure may be embodied as a system, method or computer program product. Accordingly, aspects of this disclosure may take the form of an entirely hardware embodiment, an entirely software embodiment (including firmware, resident software, micro-code, etc.), or an embodiment combining software and hardware aspects, all possibilities of which can be referred to herein as a "circuit," "module," or "system." A "circuit," "module," or "system" can include one or more portions of one or more separate physical hardware and/or software components that can together perform the disclosed function of the "circuit," "module," or "system", or a "circuit," "module," or "system" can be a single self-contained unit (e.g., of hardware and/or software). Furthermore, aspects of this disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of this disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the this disclosure may be described above with reference to flowchart illustrations and/or block diagrams of methods, apparatus (systems) and computer program products according to embodiments of this disclosure. It will be understood that each block of any flowchart illustrations and/or block diagrams, and combinations of blocks in any flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in any flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

Any suitable combination(s) of any disclosed embodiments and/or any suitable portion(s) thereof are contemplated herein as appreciated by those having ordinary skill in the art.

Those having ordinary skill in the art understand that any numerical values disclosed herein can be exact values or can be values within a range. Further, any terms of approximation (e.g., "about", "approximately", "around") used in this disclosure can mean the stated value within a range. For example, in certain embodiments, the range can be within (plus or minus) 20%, or within 10%, or within 5%, or within 2%, or within any other suitable percentage or number as appreciated by those having ordinary skill in the art (e.g., for known tolerance limits or error ranges).

The embodiments of the present disclosure, as described above and shown in the drawings, provide for improvement in the art to which they pertain. While the subject disclosure includes reference to certain embodiments, those skilled in the art will readily appreciate that changes and/or modifications may be made thereto without departing from the spirit and scope of the subject disclosure.

What is claimed is:

1. A method for determining quality of an additively manufactured article or batch thereof, comprising:
   torsion testing at least one additively manufactured test article that is built on and attached to a build plate while the at least one test article is still attached to the build plate.

2. The method of claim 1, wherein torsion testing includes applying a torque to the test article using a torsion testing machine while the build plate is retained in the torsion testing machine.

3. The method of claim 2, further comprising removing the build plate from an additive manufacturing machine and inserting the build plate into the torsion testing machine.

4. The method of claim 3, further comprising retaining the build plate in the torsion testing machine.

5. The method of claim 1, further comprising additively manufacturing the at least one test article on the build plate to have a test head configured to be torqued by a socket.

6. The method of claim 5, wherein the test head includes a hex shape.

7. The method of claim 6, wherein the at least one test article includes a narrow body.

8. The method of claim 2, further comprising sensing a torque on the at least one test article and/or a twist on the at least one test article to create torque data and/or twist data.

9. The method of claim 8, further comprising comparing the torque data and/or twist data to known expected data to determine a quality of the at least one test article.

10. The method of claim 9, further comprising plotting and displaying torque versus twist on an electronic display.

11. The method of claim 1, comprising torsion testing the at least one test article until the at least one test article breaks.

12. The method of claim 11, further comprising catching debris from the broken test article in a part catching tray.

13. The method of claim 1, wherein torsion testing the at least one additively manufactured test article is performed while the build plate is still in an additive manufacturing machine.

14. The method of claim 13, wherein torsion testing the at least one additively manufactured test article is performed prior to completion of additive manufacture of the additively manufactured article or batch thereof in the additive manufacturing machine.

* * * * *